United States Patent [19]

Laghi

[11] Patent Number: 5,443,525
[45] Date of Patent: Aug. 22, 1995

[54] CONDUCTIVE PATCH FOR CONTROL OF PROSTHETIC LIMBS

[76] Inventor: Aldo A. Laghi, 13 Meridian La., Ballston Lake, N.Y. 12019

[21] Appl. No.: 266,042

[22] Filed: Jun. 27, 1994

[51] Int. Cl.$^6$ .............................................. A61F 2/70
[52] U.S. Cl. .................................... 623/25; 623/36; 128/639; 128/644; 607/148; 607/152
[58] Field of Search ............. 623/25, 36; 128/639, 128/733, 644; 607/152, 148

[56] References Cited

U.S. PATENT DOCUMENTS

| | | | |
|---|---|---|---|
| 3,735,425 | 5/1973 | Hoshall et al. | 623/25 |
| 4,030,141 | 6/1977 | Graupe | 623/25 |
| 4,314,379 | 2/1982 | Tanie et al. | 625/25 |
| 4,521,924 | 6/1985 | Jacobsen et al. | 623/25 |
| 4,619,266 | 10/1986 | Hodgson | 128/733 |
| 4,623,354 | 11/1986 | Childress et al. | 623/25 |
| 4,926,879 | 5/1990 | Sevrain et al. | 607/152 |
| 4,964,411 | 10/1990 | Johnson et al. | 128/733 |
| 5,263,481 | 11/1993 | Axelgaard | 128/639 |
| 5,299,572 | 4/1994 | Chen et al. | 128/639 |
| 5,341,813 | 8/1994 | Teare et al. | 128/733 |

OTHER PUBLICATIONS

"Electromyographic sensor design for use with an externally powered prosthetic arm" R. L. Konigsberg.

*Primary Examiner*—David H. Willse
*Assistant Examiner*—Bruce Snow
*Attorney, Agent, or Firm*—Joseph C. Mason, Jr.; Ronald E. Smith

[57] ABSTRACT

Myoelectric control of a prosthetic limb is achieved by positioning a soft, flexible pad on the interior surface of a liner and embedding a large plurality of electrically conductive contacts within the pad. A window is cut in the liner to enable attachment of limb control electrodes to the pad. The pad has a low resistivity so that the individual contacts detect very low myoelectric signals. In a preferred embodiment, about forty thousand contacts, each of which is surrounded by non-conductive silicone, are positioned in a one inch square area. The number of signals produced enables the development of highly versatile prosthetic limbs.

4 Claims, 1 Drawing Sheet

CONDUCTIVE PATCH FOR CONTROL OF PROSTHETIC LIMBS

BACKGROUND OF THE INVENTION

1. Field of the Invention

This invention relates, generally, to control devices for prosthetic limbs. More particularly, it relates to a myoelectric control device having thousands of electrically conductive contacts for controlling a versatile prosthesis.

2. Description of the Prior Art

Early prosthetic devices intended to replace the human hand were mere hooks that had limited utility. Modern devices, however, are not much better. Typically, they include a pair of mechanical fingers and an opposable mechanical thumb that can perform a slow grasping action or a fast grasping action. The fingers and thumb are myoelectrically controlled, i.e., they receive electrical signals from electrodes placed on the patient's skin. These electrodes are sensitive to galvanic currents on the skin generated by muscles lying below the surface thereof. Thus, if an amputee quickly contracts his grasping muscles because he wants to grab something quickly, the electrodes can distinguish the electrical signals thereby generated from the signals that would be generated if a more casual contracting of the grasping muscles was made. In this manner, the amputee can select between the two rates of closing of the fingers and the opposable thumb.

Only three electrodes are employed in the above-described well known device, because the structure of the artificial hand and its abilities are so simple and limited. Each electrode is about three-eighths of an inch in diameter and is of metallic construction. Due to the size and metallic structure of the electrodes, it is not a simple task to maintain them in their proper position relative to the patient's skin. As the residual limb changes in size due to water retention or other factors throughout the day, or from day to day and month to month, the contact between the electrodes and the skin is affected; poor contact results in poor performance of the artificial hand.

There is a need, then, for an improved myoelectric control device. The improved device would have more than three electrodes so that better prosthetic hands could be developed. Moreover, the improved device would be mountable in such a way as to remain in full contact with an amputee's skin at all times the prosthetic device is worn.

However, at the time the present invention was made, it was not obvious to those of ordinary skill in this art how the needed improvements could be made, in view of the prior art when considered as a whole.

SUMMARY OF THE INVENTION

The longstanding but heretofore unfulfilled need for an improved myoelectric control device for prosthetic limbs has now been fulfilled.

The device is provided in the form of a pad that is nonmetallic, soft, and flexible. Accordingly, it may be bonded to a socket liner of any kind; thus, it remains in comfortable contact with the patient's skin all the time, even when the limb changes in size, thereby assuring reliable myoelectric control of the prosthetic device.

The novel pad includes an electrically conductive grid including a very large plurality of densely packed electrical contacts embedded within a nonconductive silicone rubber matrix. The device has the appearance and feel of a soft pad and may be provided in any desired size. The pad is preferably bonded to the interior surface of a silicone suction socket, a silicone prosthesis liner, or any other liner so that it is in direct, conforming, nonmigrating contact with the amputee's skin at a precise location on the residual limb. The pad detects very slight myoelectric currents because its resistivity is less than 0.001 ohm-cm. Each contact within the grid has a size of about 0.002 inches square and the contacts are spaced about 0.005 inches apart, measured between centers. Thus, a one inch square grid contains about forty thousand discrete contacts.

The high density of conductors and the ease of conforming the pad to the body, together with the ability to place several pads at specific locations on an amputee's residual limb, allow the detection of multitude of myoelectric impulses. The accuracy of the detection of such signals, the reliability of such detection, and the reproducibility of such detection allows a control system to sort through and organize the complex myoelectric signals, thereby enabling the development of a control system capable of producing a very complete range of motions in a prosthetic hand or other prosthetic device.

Moreover, the ability of the novel pad to detect a multitude of myoelectric signals and their intensity with a high degree of accuracy enables the development of an operating system for a control unit that could not only detect specific signals and their intensity, but which could also analyze their sequence and concurrence to allow the amputee to employ natural muscular contractions to control complex limb movements. An intelligent operating system could be developed that would be capable of learning, i.e., it could learn limb motions on the basis of an individual's preference in performing muscular contractions.

It is therefore clear that a primary object of this invention is to provide a pioneering breakthrough in myoelectric control systems by eschewing the large, metallic electrodes now in use and supplanting them with thousands of tiny electrodes embedded in a soft, flexible pad that can be placed in comfortable, nonmigrating relation to a patient's skin.

A closely related object is to enable others to develop prosthetic devices having a much wider range of motion than the currently available devices, by providing thousands of reliable control signals for controlling a versatile prosthetic device.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
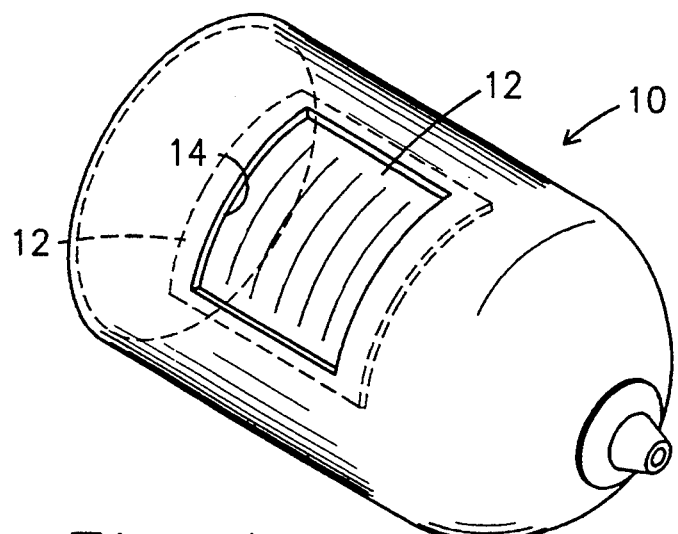
FIG. 1 is a perspective view showing a prosthesis liner equipped with the novel pad.

Referring now to FIG. 1, it will there be seen that a prosthesis liner with which the invention may be used is denoted as a whole by the reference numeral 10. Liner 10 may be a common sock made of fabric, or it may be formed of numerous other materials. In a preferred embodiment, liner 10 is made of silicone. Pad or grid 12 is bonded to an interior surface of the liner as shown, and an opening or window 14 is formed in said liner to expose it to the environment exterior to the liner. Specifically, window° 14 enables the attachment to the pad of control electrodes from the prosthetic hand (not shown). As mentioned earlier, the present invention enables the provision of a very sophisticated prosthetic hand, but such hand is not a part of this invention.

When a silicone suction socket such as liner 10 is employed as the interface between the residual limb and the prosthesis, it should be apparent that pad 12 will not migrate. Moreover, in view of the soft, silicone structure of said pad 12, it should be clear that said pad conforms to the contour of the skin and causes no discomfort of the kind that may be experienced with metallic electrodes.

Figure 2:
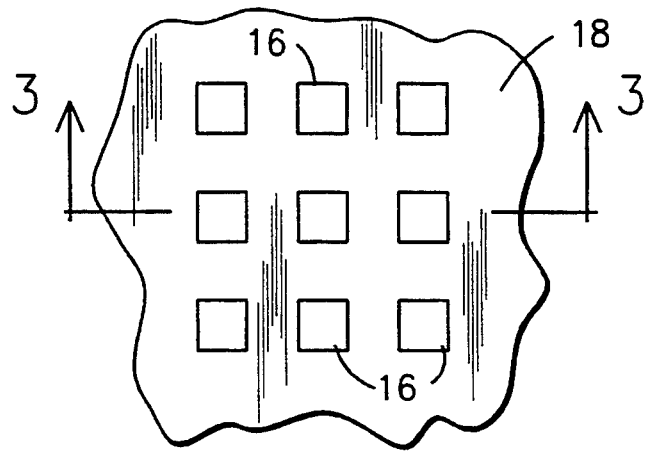
FIG. 2 is a top plan view of the pad, shown greatly magnified.
Figure 3:
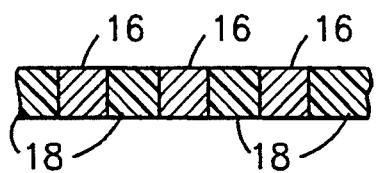
FIG. 3 is a sectional view taken along line 3—3 in FIG. 2.

FIGS. 2 and 3 depict pad 12 when greatly magnified. The individual electrodes are collectively denoted 16. As mentioned earlier, forty thousand of them may fit within a one inch square because they are about 0.002 inches square and are spaced about 0.005 inches on center from one another. Each contact 16 is made of a mixture of silicon and carbon, or silicone and silver, (or other suitable conductive mixture). Typically, the silicone and silver mixture is about eighty five percent (85%) silver by weight and fifteen percent (15%) silicone by weight. A suitable silicone and carbon mixture is about forty percent (40%) carbon by weight and sixty percent (60%) silicone by weight. Electrical contacts made of silicone and carbon mixtures, or silicone and another suitable conductor, have heretofore been known and used. For example, they are used in the nonanalogous art of wristwatches to provide electrical connections between a battery and miscellaneous electrical components where it is desired to avoid the use of soldering or other more conventional electrical connections. They are commonly known as "zebras" because they include alternating strips of conducting and non-conducting material.

Novel pad 12, however, does not include such stripes, each contact 16 being surrounded by non-conductive silicone 18 as shown.

This invention is clearly new and useful. Moreover, it was not obvious to those of ordinary skill in this art at the time it was made, in view of the prior art considered as a whole as required by law.

This invention pioneers the art of precision myoelectric control devices. Accordingly, the claims that follow are entitled to broad interpretation, as a matter of law, to protect from piracy the heart or essence of this breakthrough invention.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A myoelectric control device, comprising:
   a silicone pad of soft, flexible construction;
   said silicone pad being bonded to an interior surface of a silicone liner that provides a non-slip interface between a residual limb and a prosthesis socket;
   a window formed in said silicone liner to enable attachment of control electrodes to said silicone pad;
   said silicone pad having a plurality of electrically conductive contacts embedded in a non-conductive silicone matrix;
   said electrically conductive contacts being made of a silicone/conductor mixture;
   said electrically conductive contacts being arranged in a grid pattern throughout said silicone pad; and
   each of said electrically conductive contacts having a low resistivity for detecting low strength myoelectric signals;
   whereby said electrically conductive contacts collectively supply signals that may be employed to control movements of a prosthetic hand.

2. The device of claim 1, wherein each of said electrically conductive contacts is about 0.002 inches square.

3. The device of claim 2, wherein said electrically conductive contacts are spaced apart from one another by about 0.005 inches when measured between centers thereof.

4. The device of claim 1, wherein said low resistivity is about 0.001 ohm-cm.

* * * * *